United States Patent
Carlson et al.

(10) Patent No.: US 9,993,301 B2
(45) Date of Patent: Jun. 12, 2018

(54) METHOD AND SYSTEM FOR MONITORING A REPROCESSING DEVICE FOR ENDOSCOPES

(71) Applicant: OLYMPUS WINTER & IBE GMBH, Hamburg (DE)

(72) Inventors: Torben Carlson, Hamburg (DE); Henning Thate, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 316 days.

(21) Appl. No.: 14/863,826

(22) Filed: Sep. 24, 2015

(65) Prior Publication Data
US 2016/0008079 A1    Jan. 14, 2016

Related U.S. Application Data

(63) Continuation of application No. PCT/EP2014/000606, filed on Mar. 10, 2014.

(30) Foreign Application Priority Data

Mar. 26, 2013  (DE) .................. 10 2013 205 296

(51) Int. Cl.
*A61B 1/12*    (2006.01)
*A61B 19/00*   (2006.01)
*A61B 90/70*   (2016.01)

(52) U.S. Cl.
CPC .............. *A61B 19/34* (2013.01); *A61B 1/123* (2013.01); *A61B 90/70* (2016.02); *A61B 2090/701* (2016.02); *A61B 2090/702* (2016.02)

(58) Field of Classification Search
CPC combination set(s) only.
See application file for complete search history.

(56) References Cited

U.S. PATENT DOCUMENTS

| | | |
|---|---|---|
| 5,422,276 A | 6/1995 | Colvin |
| 2003/0187586 A1 | 10/2003 | Katzenmaier et al. |
| 2005/0033464 A1 | 2/2005 | Nguyen |

(Continued)

FOREIGN PATENT DOCUMENTS

| | | |
|---|---|---|
| CN | 1854719 A | 11/2006 |
| CN | 101300034 A | 11/2008 |

(Continued)

OTHER PUBLICATIONS

Japanese Office Action dated May 16, 2017 in Japanese Patent Application No. 2016-504510.

(Continued)

*Primary Examiner* — Mamadou Diallo
(74) *Attorney, Agent, or Firm* — Scully, Scott, Murphy & Presser, P.C.

(57) ABSTRACT

A method for monitoring a reprocessing device for endoscopes the method including: logging one or more process parameters as well as a time of each reprocessing operation over a plurality of reprocessing operations for at least one endoscope in at least one reprocessing device; storing the logged one or more process parameters in association with the respective reprocessing operation, and performing a trend analysis of at least one logged process parameter in an evaluation device via the one or more logged process parameters.

13 Claims, 3 Drawing Sheets

(56) References Cited

U.S. PATENT DOCUMENTS

| | | | |
|---|---|---|---|
| 2007/0100204 A1* | 5/2007 | Feld | A61B 1/00057 600/117 |
| 2009/0055215 A1* | 2/2009 | Giraldo | G06F 19/327 705/2 |
| 2009/0060798 A1* | 3/2009 | Williams | A61L 2/18 422/111 |
| 2009/0103836 A1 | 4/2009 | Shimizu et al. | |
| 2010/0191049 A1* | 7/2010 | Mandava | A61B 19/0248 600/102 |
| 2011/0236082 A1 | 9/2011 | Kobayashi et al. | |
| 2011/0318729 A1* | 12/2011 | Sutton | C12Q 1/485 435/5 |
| 2012/0204906 A1 | 8/2012 | Bommarito et al. | |
| 2017/0052190 A1* | 2/2017 | Sutton | G01N 33/581 |

FOREIGN PATENT DOCUMENTS

| | | |
|---|---|---|
| DE | 3334999 A1 | 4/1985 |
| DE | 10135137 A1 | 1/2002 |
| DE | 102011016255 A1 | 10/2012 |
| EP | 1529484 A2 | 5/2005 |
| JP | 2002-092181 A | 3/2002 |
| JP | 2006-230709 A | 9/2006 |
| JP | 2009-066290 A | 4/2009 |
| JP | 2010-075267 A | 4/2010 |
| JP | 2011-206316 A | 10/2011 |
| WO | WO 2012/033850 A2 | 3/2012 |

OTHER PUBLICATIONS

International Search Report dated May 15, 2014 issued in PCT/EP2014/000606.

* cited by examiner

METHOD AND SYSTEM FOR MONITORING A REPROCESSING DEVICE FOR ENDOSCOPES

CROSS-REFERENCE TO RELATED APPLICATION

The present application is a continuation of PCT/EP2014/000606 filed on Mar. 10, 2014, which is based upon and claims the benefit to DE 10 2013 205 296.0 filed on Mar. 26, 2013, the entire contents of each of which are incorporated herein by reference.

BACKGROUND

Field

The present application relates to a method for monitoring a reprocessing device for endoscopes, in particular a cleaning and/or disinfection device, according to which method one or more process parameters as well as a time of each reprocessing operation are logged over a plurality of reprocessing operations for at least one endoscope in at least one reprocessing device and are stored in association with the respective reprocessing operation. The present application further relates to a corresponding system for monitoring a reprocessing device for endoscopes, comprising at least one reprocessing device and at least one evaluation device.

Prior Art

High standards are set for the reprocessing of endoscopes after use, among other things in the clinical field. The reprocessing normally comprises a washing, a disinfection as well as a drying of the endoscopes. One or two wash or prewash cycles normally precede the disinfection; there are rinse cycles with clear water and drying cycles. Cleaning agents or respectively one or more chemicals for disinfecting are added for washing and disinfecting. This normally takes place in automated reprocessing devices.

A corresponding automatic or respectively automated reprocessing device is sold for example by the applicant under the manufacturer name and type designation Olympus ETD3, where ETD stands for "Endo Thermo Disinfector." This reprocessing device is equipped with different reprocessing programs and allows the simultaneous reprocessing of several flexible or rigid endoscopes. It offers disinfection with the conventionally used chemical glutaraldehyde and alternatively based on peracetic acid (PAA). Together with the PAA, an activator solution is also added. The ETD3 also comprises a UV unit, with which rinse water can be further disinfected.

The ETD3 has a comprehensive sensor system and logging functions. Thus, the quantity of the different reprocessing agents, i.e. water metering, washing agent metering and chemical metering, is recorded and logged for the reprocessing operations respectively in addition to corresponding time stamps among other things by means of rotary vane flow meters. The ETD3 also has an automatic transponder-based detection of compatible endoscopes via the EndoID system by Olympus. With this system, among other things, the serial number of the reprocessing device, type and serial number of the reprocessed endoscope, name of the operator who started the reprocessing operation and other process parameters are logged. The EndoID system makes it possible to set the process parameters for the endoscope automatically after detecting the endoscope to be reprocessed. The ETD3 also has leak detection.

In order to meet any potentially existing requirements in terms of documentation, subsequent to the reprocessing operation, a report can be generated that indicates whether all process parameters of the reprocessing operation were correct, i.e. located within a calibrated or predetermined parameter range, and that a sufficient reprocessing result has been obtained. This report can be printed or transmitted directly, for example via an ISDN or LAN connection, to an endoscope information management system. Moreover, the ETD3 offers the option of remote servicing.

SUMMARY

Based on this state of the art, an object is to improve the monitoring of reprocessing devices for endoscopes and of endoscopes.

This object can be solved by a method for monitoring a reprocessing device for endoscopes, in particular a cleaning and/or disinfection device, according to which method one or more process parameters as well as a time of each reprocessing operation are logged over a plurality of reprocessing operations for at least one endoscope in at least one reprocessing device and are stored in association with the respective reprocessing operation, which is further developed in that a trend analysis of at least one logged process parameter is performed in the evaluation device via the at least one logged process parameter.

Beyond the previously covered logging and documentation, a further data analysis with generally known statistical methods, for example linear or other regression analyses, is thus performed, with which among other things an arising servicing need for a reprocessing device can be detected early on so that suitable measures can be taken in a timely manner before reprocessing operations are performed in a non-rule- and non-specification-compliant manner due to the occurrence of non-specification-conforming process parameters, resulting in faulty reprocessing results.

Within such framework, a trend is understood as being a temporal development, but also as conspicuities which depend on other process parameters, which occur for example increasingly with particular reprocessing programs or with certain operators. In the former cases, servicings can be scheduled for example, i.e. servicings on site or, if necessary, remote servicings. In the latter case, for example, the training need of the employees can be better coordinated.

With the method, the quality of the reprocessing results as well as the efficiency of the reprocessing of endoscopes are both improved in this manner because faulty reprocessing results can already be averted before they occur upon detection of corresponding trends.

In embodiments of the method, a reprocessing device indicator, an operator indicator, a reprocessing program indicator, at least one endoscope indicator for at least one reprocessed endoscope, at least one reprocessing agent indicator, a pressure loss and/or a pressure loss speed, at least one dose quantity of at least one reprocessing agent to be metered, a start and/or end time of the reprocessing operation, a process duration, malfunctions, operating errors and/or error messages is or are logged. A reprocessing device indicator is thereby for example a serial number of the reprocessing device; an operator indicator, name or personal ID number; a reprocessing program indicator, for example a program name or a description or number identifying the reprocessing program; an endoscope indicator, a type designation and/or a serial number of an endoscope; a reprocessing agent indicator, for example a chemical name or a chemical identification. When several of these process parameters are logged and analyzed, this increases the process reliability, quality and efficiency of the endoscope reprocessing.

When partial-operation-relevant process parameters with respect to the individual partial operations are logged for reprocessing operations, in which several different partial operations are performed, in particular a partial operation identifier, duration of the reprocessing partial operation and/or dose quantities of one or more reprocessing agents to be metered during the partial operation, a closely monitored and specific trend analysis is then possible. Partial operations are, for example, prewash cycles, wash cycles, disinfection cycles, rinse cycles, dry cycles, among others things, each of which are performed with separate process parameters. Service-relevant conspicuities in individual partial operations can thus be identified and resolved.

In the trend analysis, at least one logged process parameter can be represented and/or evaluated as a function of the respective start or end times of the reprocessing operations, of the reprocessing device indicator, of the reprocessing program indicator, of the partial operation indicator, of the operator indicator and/or of the endoscope indicator.

The temporal trend analysis typically relates for example to the metering of the disinfection chemical or disinfection chemicals or other reprocessing agents. In a plurality of consecutive reprocessing operations, the chemical dose, for example, can more or less continuously decrease or increase within the permitted range. Each individual dose and the thusly achieved disinfection result are thus specification-conforming and inconspicuous. A servicing need would have previously only been identified if this trend had continued and the dose had actually drifted out of the rule-compliant range. A trend analysis according to the invention actually covers the prevalent trend so that countermeasures can be taken during a servicing before the disinfection result becomes inadequate or vice versa more disinfection chemicals are used than are needed.

An evaluation of the logged process parameter(s) as a function of the other indicators allows an identification of irregularities, which do not occur in a temporally dependent manner, but are rather typical for individual reprocessing devices, reprocessing programs, partial operations, operators or endoscopes. In this context, the logged data for the representation and/or evaluation can be filtered by the point in time, the reprocessing device indicator, the operator indicator, the reprocessing program indicator, the partial program indicator and/or the at least one endoscope indicator. A detailed trend analysis is thus realized.

An example of a use for this is the monitoring of the calibration of dosing devices in a reprocessing device. For this, the deviation of a dose quantity from the desired dose quantity for a certain dosing device can be analyzed depending on the size of the desired dose quantity. If this difference rises or falls with an increasing desired dose quantity, then the calibration of the dosing device should be adjusted.

The trend analysis can analyze whether, with time, a logged process parameter, in particular a dose quantity or a process duration, develops such that this process parameter leaves a calibrated range or a tolerance range if the trend continues. A servicing need of the reprocessing device is thereby advantageously signaled before a logged process parameter has left the calibrated range or tolerance range if the trend analysis indicates such a trend.

The need for training for an operator can also be signaled if the trend analysis shows that the frequency of malfunctions, operating errors and/or error messages is elevated for one operator compared to another operator.

A pressure loss and/or a pressure loss speed can also be an important process parameter that can be captured by the trend analysis. In some reprocessing devices, a leak test of the endoscope is performed before the start of the endoscope reprocessing. For this, slight excess pressure is generated and the pressure drop within a certain period of time is checked. If the pressure loss is above a defined threshold of a low and reliable pressure loss, then the endoscope is reported as being permeable and the reprocessing is not started. This prevents moisture from getting into sensitive parts of the endoscope during the reprocessing. Without trend analysis, a leak is always associated with the endoscope and leaks in the area of the reprocessing device are thus not reliably identified. Furthermore, an aging of both the endoscope and the reprocessing device is first identified when the trigger threshold has been reached so that a reprocessing is then no longer possible.

The trend analysis of the leak test via the pressure loss or respectively the pressure loss speed makes it possible to determine, for example through correlation with the endoscope indicator, whether a behavior changing over the trend period can be attributed to the reprocessing device or respectively its leak tester or the endoscope. An endoscope approaching a degree of leakiness to be corrected can then be registered for repair. In contrast, via an increase in the pressure loss that is independent of the endoscopes, a problem of the leak tester of the reprocessing device can be identified and communicated in a timely manner, for example saved in the service memory of the reprocessing device for a service technician.

An object is also solved by a system for monitoring a reprocessing device for endoscopes, comprising at least one reprocessing device and at least one evaluation device, in which the reprocessing device is configured to log for reprocessing operations one or more process parameters as well as a time of the respective reprocessing operation and to save it/them in correlation with the respective reprocessing operation and/or to transmit it/them to the evaluation device, which is further developed in that the evaluation device is designed and set up to perform via at least one logged process parameter a trend analysis of the at least one logged process parameter. The evaluation device can thereby also be integrated in the reprocessing device, which can thus perform a self-diagnosis by means of the trend analysis.

The system can be particularly configured and set up to perform a previously described method.

The characteristics, properties and advantages named for the methods and systems disclosed herein also apply without restriction to the respective other contemplated subject matters.

Further characteristics will become apparent from the description of embodiments together with the claims and the included drawings. Embodiments can fulfill individual characteristics or a combination of several characteristics.

BRIEF DESCRIPTION OF THE DRAWINGS

The embodiments are described below, without restricting the general idea of the invention, based on exemplary embodiments in reference to the drawings, whereby we expressly refer to the drawings with regard to the disclosure of all details that are not explained in greater detail in the text. The figures show in:

FIG. 4b illustrates an enlarged portion of FIG. 4a.

In the drawings, the same or similar elements and/or parts are provided with the same reference numbers in order to prevent the item from needing to be reintroduced.

DETAILED DESCRIPTION

Figure 1:
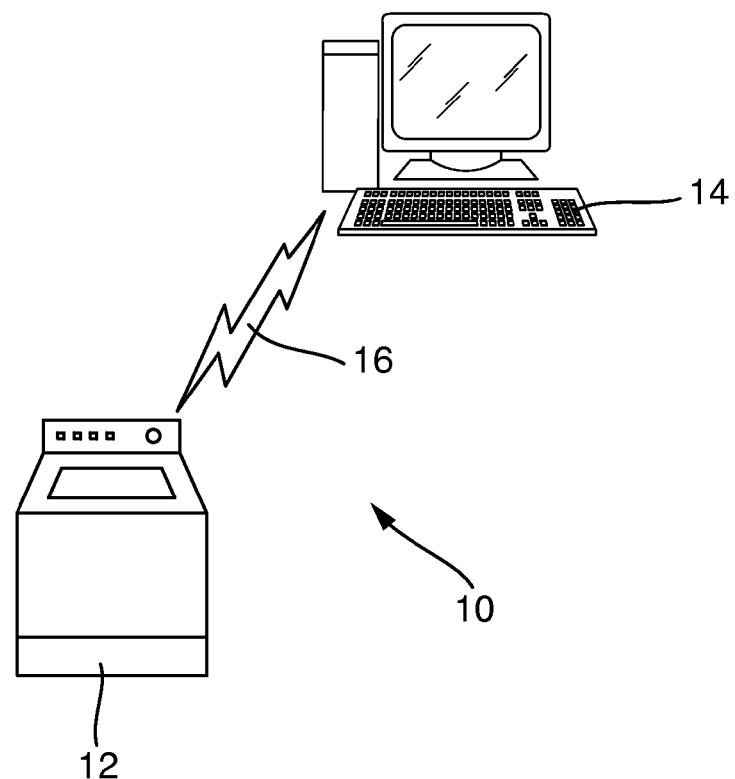
FIG. 1 illustrates a schematic representation of a system.

FIG. 1 shows a system 10 for monitoring a reprocessing device 12 for endoscopes, which comprises, in addition to the reprocessing device 12, an evaluation device 14. The reprocessing device 12 and the evaluation device 14 are interconnected via a data connection 16, for example an ISDN connection or LAN connection. In this manner, a remote servicing of the reprocessing device 12 can take place by means of the evaluation device 14 and the reprocessing device 12 can transmit log data to the evaluation device 14.

The reprocessing device 12 can be, for example, the automatic reprocessing device ETD3 of the applicant. Alternatively, the evaluation device 14 can also be integrated in the reprocessing device 12. However, a data connection 16 to an external evaluation device 14 can also be present in this case.

The reprocessing device 12 serves to clean and disinfect endoscopes after use. The reprocessing device 12 thereby runs through several reprocessing operations, such as for example prewash cycle, wash cycle, disinfection cycle, rinse cycle and dry cycle. Additional cycles can also be included, such as for example diagnostics cycles for the endoscopes, e.g., a leak test.

The reprocessing device 12 is designed to log, using its sensor system, different process parameters, such as for example the identity of the operator, the identity of the reprocessed endoscopes as well as partial operation durations, total duration, quantities of the metered-in reprocessing agents, like water, chemicals, cleaning agent, etc. and to transmit this log to the evaluation device 14. The evaluation device 14 is designed to create a trend analysis using this data via a plurality of reprocessing operations in order to be able to detect early, for example, a servicing need for the machine or a training need for operators.

Figure 2:
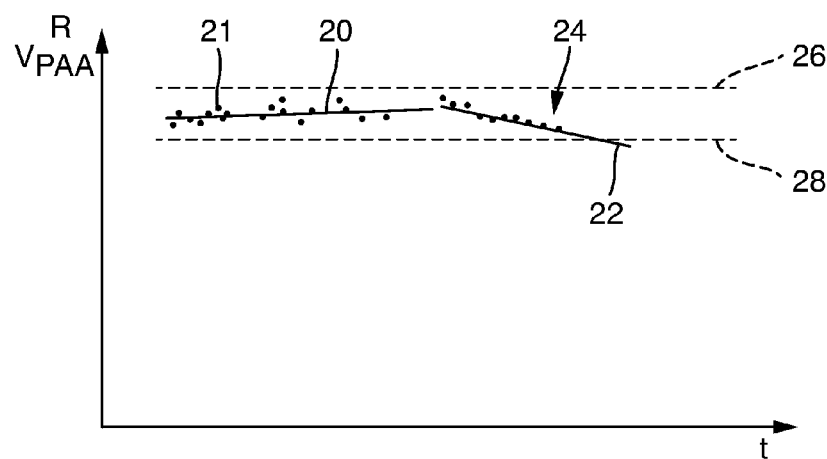
FIG. 2 illustrates a graphical representation of a trend analysis.
Figure 3:
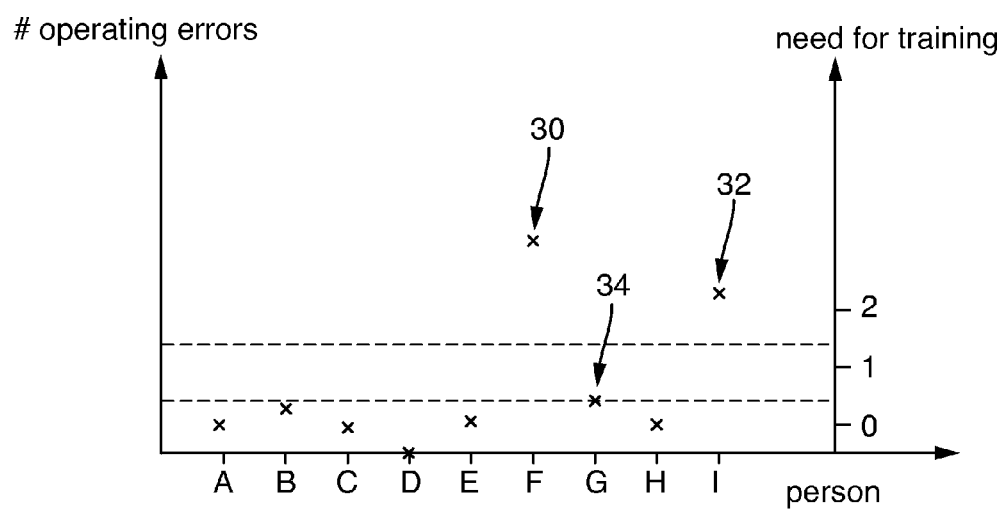
FIG. 3 illustrates a graphical representation of a further trend analysis.

Several examples of possible trend analyses within the framework of the invention are shown in FIGS. 2 to 4.

FIG. 2 shows a trend analysis for a dosing parameter, namely the temporal progression over a total of 27 reprocessing operations of the metering of peracetic acid (PAA). The data points 21 correspond respectively to one reprocessing operation. The parameter $V_{PAA}^R$ describes the actually released PAA quantity during a reprocessing operation or respectively a disinfection partial operation of a reprocessing operation. The progression of time (t) is shown on the x axis. The permissible range for the data points 21 is limited by an upper limit 26 and a lower limit 28. Measurement values outside of this range lead to error messages and to inadequate disinfection results.

The trend analysis shows that the measured values 21 are first located in a middle range of the permissible range without a critical trend being detectable. The (linear) trend 20 is uncritical in this case. However, as of approximately half of the measurement time, a critical trend 24 does develop, in which the individual measurement values 21 move systematically towards the lower limit 28 of the permissible range. It would be anticipated that, in further reprocessing operations, the actually released dose quantity of PAA would drop below the lower limit 28 and lead to inadequate disinfection results. This trend 22 was identified at time 24 so that a servicing command or a servicing request can be issued. An onsite servicing or a remote servicing is then performed on short notice, in order to fix the problem, which leads to the critical trend 22. There will thus be no reprocessing operations for those where the released quantity of PAA lies below the lower limit 28.

FIG. 3 shows a different type of trend analysis, namely a person-related trend analysis. Here, it is recorded for persons A to I how many operating errors were caused by operators A to I or what their operating error rate was. For persons A, B, C, D, E and H, the number of operating errors or respectively the operating error rate is so low that it falls into the range of zero in terms of need for training so that these persons do not need training. Two persons, namely F and I, have such high numbers or respectively rates of operating errors 30, 32 that they have a high and urgent need for training of category 2. These persons must be promptly retrained. Another person G has a slightly increased number or respectively rate of operating errors 34 so that it must be considered whether or not this person needs further training. This person G falls into the lower range of range 1 for need for training.

The operating error rate can also be represented in a further trend analysis for individual persons over time so that it can be determined, if necessary, when new trainings should be offered for these persons due to their worsening operating error rates. The need for training for the entire staff can thus be coordinated.

Instead of operating errors, the number of operating errors and other potentially person-related indicators can also be analyzed.

Figure 4A:
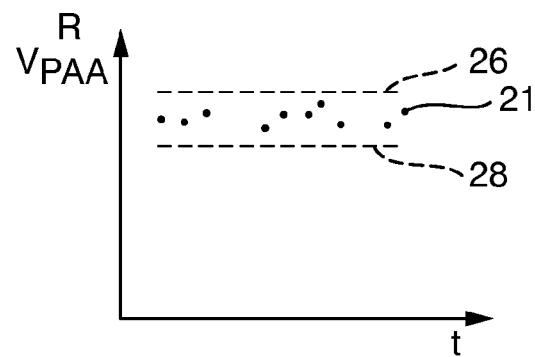
FIG. 4a illustrates a graphical representation of a further trend analysis.

FIG. 4a shows graphically a further trend analysis. As illustrated in FIG. 4a shows the actually released PAA quantity $V_{PAA}^R$ against a program-appropriate PAA quantity $V_{PAA}^P$. In this case, three different programs or respectively partial programs $P_1$, $P_2$ and $P_3$ are shown on the x axis, i.e. the axis for $V_{PAA}^P$, for which respectively a different quantity need for PAA exists, i.e. respectively different dose quantities are released. The required dose quantity in program $P_1$ is low, in program $P_2$ medium-high and in program $P_3$ high. It can also concern the number of one, two or three endoscopes to be reprocessed in the reprocessing device 12, whereby the need for PAA is scaled accordingly. Reference number 40 indicates a target calibration, which linearly connects the target values with each other. Ideally, with correct calibration, the respectively actually released quantity $V_{PAA}^R$ would thus be equal to the target quantity $V_{PAA}^P$ for the individual programs $P_1$, $P_2$ and $P_3$.

Figure 4B:
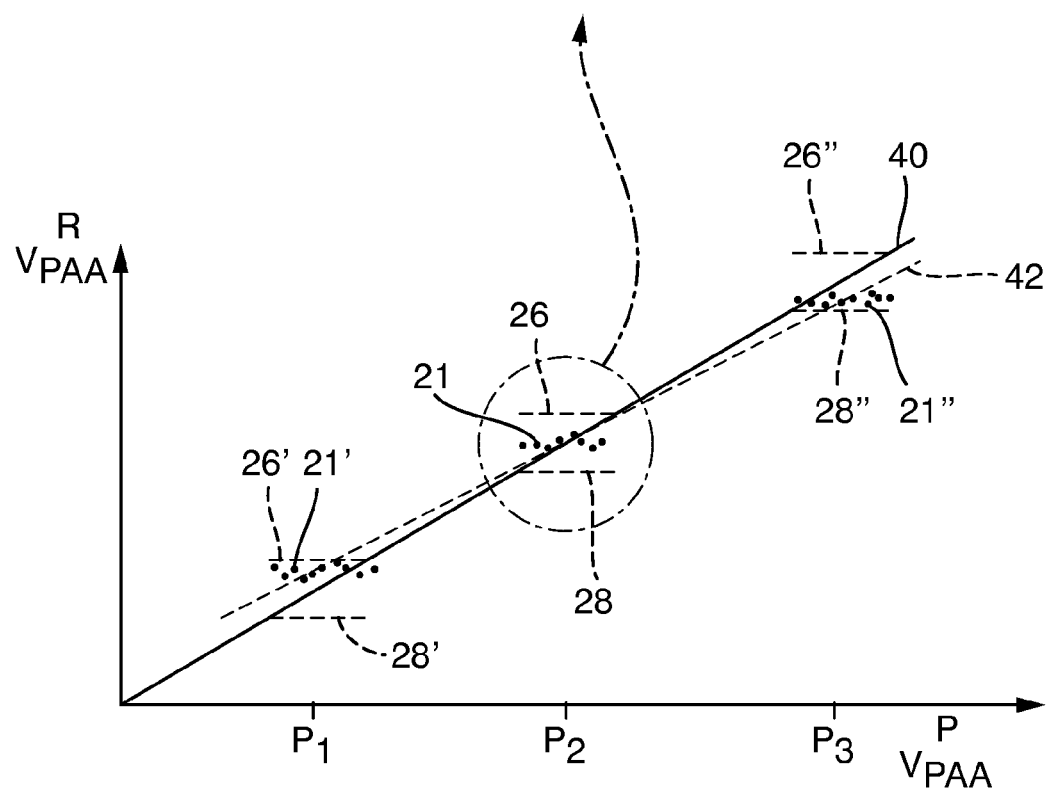

Data points 21, 21' and 21" are shown respectively for programs $P_1$, $P_2$ and $P_3$. As can be seen in FIG. 4b, illustrating a sectional enlargement of the middle part of FIG. 4a, these data points 21, 21', 21" are applied respectively against a time axis so that the calibration trend analysis can also be combined with a temporal trend analysis. Each individual data sequence 21, 21', 21" thus mainly corresponds with a temporal trend analysis shown in FIG. 2.

As results from FIGS. 4a and 4b, there is a faulty calibration. The data points 21 for the middle program $P_2$ lie in the middle of the permissible range between the upper limit 26 and the lower limit 28. For the program $P_1$ with little need for PAA, the data points 21' lie near the upper limit 26' of the range between the upper limit 26' and the lower limit 28'. Conversely, a data sequence with data points 21", which lie near the lower limit 28" of the applicable range between the upper limit 26" and the lower limit 28", results for program P₃ with a high need for PAA. There is thus a trend towards a systematic overdose in the case of small amounts and a systematic underdose in the case of large amounts. This is described by an interpolated actual calibration line 42, which has a lower slope than the target calibration line 40. The data points 21, 21' and 21" can be summarized respectively in one point or respectively one distribution, in order to correctly determine the calibration. But a temporal analysis of the change in the calibration can also take place. If such a faulty calibration is identified by the trend analysis shown in FIGS. 4a and 4b, measures can be taken to fix this faulty calibration, for example within the framework of a remote servicing or an onsite servicing.

All named characteristics, including those taken from the drawings alone and also individual characteristics which are disclosed in combination with other characteristics are considered alone and in combination as essential for the invention. Embodiments can be realized by individual characteristics, or a combination of several characteristics.

LIST OF REFERENCE NUMBERS

10 System
12 Reprocessing device
14 Evaluation device
16 Data connection
20 Uncritical trend
21-21" Data on doses
22 Critical trend
24 Time of servicing command
26-26" Upper limit of the permissible range
28-28" Lower limit of the permissible range
30 Number of operating errors, person F
32 Number of operating errors, person I
34 Number of operating errors, person G
40 Target calibration
42 Actual calibration
t Time
$V_{PAA}^R$ Actually released PAA quantity
$V_{PAA}^P$ Program-appropriate PAA quantity

What is claimed is:

1. A method for monitoring a reprocessing device for reprocessing one or more endoscopes, the method comprising:
    controlling the reprocessing device to perform a plurality of reprocessing operations over time on the one or more endoscopes;
    controlling a sensor system to sense a plurality of values of at least one process parameter under which each of the plurality of reprocessing operations is performed over time;
    logging each of the plurality of values of the at least one process parameter with a corresponding time that the each of the plurality of reprocessing operations was performed;
    determining a trend of the plurality of values of the at least one process parameter logged with the corresponding times;
    performing a comparison of a value of the trend to one or more predetermined values to determine whether a value of the at least one process parameter will be outside of a predetermined operation range in a reprocessing operation to be performed in the future; and
    controlling an output device to signal a determination that the value of the at least one process parameter will be outside of the predetermined operation range in the reprocessing operation to be performed in the future based on a result of the comparison of the value of the trend to the one or more predetermined values.

2. The method according to claim 1,
    wherein the at least one process parameter is or are selected from a group consisting of a reprocessing device indicator, an operator indicator, a reprocessing program indicator, at least one endoscope indicator for at least one reprocessed endoscope, at least one reprocessing agent indicator, a pressure loss and/or a pressure loss speed, at least one dose quantity of at least one reprocessing agent to be metered, a start of the reprocessing operation, an end time of the reprocessing operation, a process duration, malfunctions, operating errors and error messages.

3. The method according to claim 1,
    wherein the logging comprises, for reprocessing operations in which several different partial operations are performed, logging partial-operation-relevant process parameters with respect to the individual partial operations.

4. The method according to claim 3,
    wherein the partial-operation-relevant process parameters are selected from a group consisting of a partial operation identifier, a duration of the reprocessing partial operation and dose quantities of one or more reprocessing agents to be metered during the partial operation.

5. The method according to claim 1,
    wherein determining the trend comprises, one or more of representing and evaluating at least one logged process parameter as a function of one or more of a respective start or end time of the plurality of reprocessing operations, of a reprocessing device indicator, of a reprocessing program indicator, of a partial operation indicator, of an operator indicator and of the endoscope indicator.

6. The method according to claim 5, further comprising filtering one or more of logged data for the representation and/or evaluation by a point in time, the reprocessing device indicator, the operator indicator, the reprocessing program indicator, the partial program indicator and the endoscope indicator.

7. The method according to claim 4,
    wherein performing the comparison of the value comprises performing a comparison of a value of the trend to a calibrated range or a tolerance range to determine whether the value of the at least one process parameter will be outside of the calibrated range or the tolerance range in the reprocessing operation to be performed in the future.

8. The method according to claim 7,
    wherein the logged process parameter is one of a dose quantity or a process duration.

9. The method according to claim 7,
    wherein controlling the output device comprises controlling the output device to signal a servicing need of the reprocessing device before the value of the at least one process parameter is outside of the calibrated range or tolerance range if the result of the comparison indicates such a trend.

10. The method according to claim 1,
    wherein controlling the output device comprises controlling the output device to signal a need for training for an operator if the result of the comparison shows that one or more of a frequency of malfunctions, operating errors and error messages is elevated for one operator compared to other operators.

11. The method of claim 1,
wherein the reprocessing device is a cleaning and/or disinfection device.

12. A system for monitoring a reprocessing device for reprocessing one or more endoscopes, the system comprising:
a processor comprising hardware, wherein the processor is configured to:
control the reprocessing device to perform a plurality of reprocessing operations over time on the one or more endoscopes;
controlling a sensor system to sense a plurality of values of at least one process parameter under which each of the plurality of reprocessing operations is performed over time;
logging each of the plurality of values of the at least one process parameter with a corresponding time that the each of the plurality of reprocessing operations was performed;
determining a trend of the plurality of values of the at least one process parameter logged with the corresponding times;
performing a comparison of a value of the trend to one or more predetermined values to determine whether a value of the at least one process parameter will be outside of a predetermined operation range in a reprocessing operation to be performed in the future; and
controlling an output device to signal a determination that the value of the at least one process parameter will be outside of the predetermined operation range in the reprocessing operation to be performed in the future based on a result of the comparison of the value of the trend to the one or more predetermined values.

13. The system according to claim 12,
wherein the processor is integrated in the reprocessing device.

* * * * *